(12) United States Patent
Wei et al.

(10) Patent No.: US 10,067,042 B2
(45) Date of Patent: Sep. 4, 2018

(54) LIQUID ANALYZING DEVICE

(71) Applicant: SKYLA CORPORATION HSINCHU SCIENCE PARK BRANCH, Hsinchu (TW)

(72) Inventors: Chia-Chun Wei, Taipei (TW); Hung-Wei Chen, Taipei (TW)

(73) Assignee: SKYLA CORPORATION HSINCHU SCIENCE PARK BRANCH, Hsinchu (TW)

(*) Notice: Subject to any disclaimer, the term of this patent is extended or adjusted under 35 U.S.C. 154(b) by 121 days.

(21) Appl. No.: 15/196,049

(22) Filed: Jun. 29, 2016

(65) Prior Publication Data
US 2017/0307487 A1 Oct. 26, 2017

(30) Foreign Application Priority Data
Apr. 20, 2016 (CN) .......................... 2016 1 0248092

(51) Int. Cl.
*G01N 21/75* (2006.01)
*G01N 1/38* (2006.01)
(Continued)

(52) U.S. Cl.
CPC .................. *G01N 1/38* (2013.01); *B01F 7/26* (2013.01); *B01F 9/00* (2013.01); *B01F 15/00435* (2013.01); *B01L 3/502* (2013.01); *B04B 5/0407* (2013.01); *G01N 33/49* (2013.01); *G01N 35/00* (2013.01); *B01F 2015/00629* (2013.01);
(Continued)

(58) Field of Classification Search
CPC .......... G01N 1/38; G01N 35/00; G01N 33/49; G01N 2035/00524; G01N 2035/00495; G01N 2001/386; B01F 7/26; B01F 15/00435; B01F 9/00; B01F 2015/00629; B01F 2215/0037; B01L 3/502; B01L 2400/0409; B01L 2200/06; B01L 2300/0803; B01L 2300/123; B01L 2300/0609; B04B 5/0407; F16H 19/003
See application file for complete search history.

(56) References Cited

U.S. PATENT DOCUMENTS 5,089,417 A 2/1992 Wogoman
5,789,259 A * 8/1998 Wardlaw ............... B01L 3/5021
366/213

FOREIGN PATENT DOCUMENTS

CN 103807396 5/2014
CN 204216571 3/2015
(Continued)

OTHER PUBLICATIONS

"Search Report of Europe Counterpart Application", dated May 2, 2017, p. 1-p. 10.

*Primary Examiner* — Dennis White
(74) *Attorney, Agent, or Firm* — JCIPRNET (57) ABSTRACT

A liquid analyzing device includes a carrier, a driving unit, a rotating plate and a transmission mechanism. The driving unit is adapted to drive the carrier to rotate. The rotating plate is rotatably disposed on the carrier and adapted to support an analyzing cassette. The transmission mechanism is connected between the carrier and the rotating plate. When the driving unit drives the carrier to rotate to enable a rotation speed of the carrier to be changed and cross a predetermined rotation speed, the rotating plate rotates relatively to the carrier.

7 Claims, 7 Drawing Sheets (51) Int. Cl.
*B01F 7/26* (2006.01)
*B01F 15/00* (2006.01)
*B01L 3/00* (2006.01)
*B01F 9/00* (2006.01)
*B04B 5/04* (2006.01)
*G01N 33/49* (2006.01)
*G01N 35/00* (2006.01)
*F16H 19/00* (2006.01)

(52) U.S. Cl.
CPC ... *B01F 2215/0037* (2013.01); *B01L 2200/06* (2013.01); *B01L 2300/0609* (2013.01); *B01L 2300/0803* (2013.01); *B01L 2300/123* (2013.01); *B01L 2400/0409* (2013.01); *F16H 19/003* (2013.01); *G01N 2001/386* (2013.01); *G01N 2035/00495* (2013.01); *G01N 2035/00524* (2013.01)

(56) References Cited

FOREIGN PATENT DOCUMENTS

| WO | 0029121 | 5/2000 | |
|----|---------|--------|---|
| WO | 2015181725 | 12/2015 | |
| WO | WO-2015181725 A1 * | 12/2015 | ............. B01L 9/527 |

* cited by examiner

LIQUID ANALYZING DEVICE

CROSS-REFERENCE TO RELATED APPLICATION

This application claims the priority benefit of China application serial no. 201610248092.4, filed on Apr. 20, 2016. The entirety of the above-mentioned patent application is hereby incorporated by reference herein and made a part of this specification.

BACKGROUND

Field of the Invention

The invention relates to an analyzing device and more particularly, to a liquid analyzing device.

Description of Related Art

In clinical tests of liquid components, taking blood components as an example, various types of blood analyzing devices can be used for analyzing the blood. In one type of the blood analyzing devices, an analyzing cassette is placed on a carrier of the blood analyzing device after the blood and medicaments are contained in the analyzing cassette, and the carrier is driven to rotate, such that the blood and the medicaments in the analyzing cassette are mixed to produce a chemical reaction, and thereby, the blood is analyzed by means of optical detection. In this type of blood analyzing device, when the analyzing cassette is placed on the carrier of the blood analyzing device, the analyzing cassette is immovable related to the carrier, and therefore, when the carrier starts to rotate and to drive the analyzing cassette to rotate, the blood in the analyzing cassette is affected by a centrifugal force in one direction and flow toward a direction related to the analyzing cassette.

In this type of blood analyzing device, for sufficiently mixing the blood and the medicaments, the carrier usually has to be switched from a rotation state to a static state, then the analyzing cassette is manually removed, changed to another direction, and placed on the carrier again to change its facing direction, and thereafter, the carrier is driven to rotate again, such that the blood in the analyzing cassette can flow toward another direction related to the analyzing cassette through changing the facing direction of the analyzing cassette, thereby, effectively improving the efficiency of mixing the blood and the medicaments. However, the manner causes the increase to the operation time.

SUMMARY

The invention provides a liquid analyzing device including a carrier, a driving unit, a rotating plate and a transmission mechanism. The driving unit is adapted to drive the carrier to rotate. The rotating plate is rotatably disposed on the carrier and adapted to support an analyzing cassette. The transmission mechanism is connected between the carrier and the rotating plate. When the driving unit drives the carrier to rotate to enable a rotation speed of the carrier to be changed and cross a predetermined rotation speed, the rotating plate rotates relatively to the carrier.

In an embodiment of the invention, when the driving unit drives the carrier to be changed from a first rotation speed to a second rotation speed or from the second rotation speed to the first rotation speed, the rotating plate rotates relatively to the carrier. The predetermined rotation speed is between the first rotation speed and the second rotation speed.

In an embodiment of the invention, when the carrier is changed from the first rotation speed to the second rotation speed, the rotating plate rotates relatively to the carrier along a first direction; and when the carrier is changed from the first rotation speed to the second rotation speed, the rotating plate rotates relatively to the carrier along a second direction. The second direction is opposite to the first direction.

In an embodiment of the invention, the transmission mechanism includes an elastic member. When the rotation speed of the carrier is less than the predetermined rotation speed, the elastic member has a first deformed state, and the carrier is in a first facing state. When the rotation speed of the carrier is greater than the predetermined rotation speed, the elastic member has a second deformed state, and the carrier is in a second facing state. The second facing state refers to the rotating plate rotating relatively to the carrier for an angle from the first facing state, and the second deformed state refers to the elastic member being deformed by a deformation amount from the first deformed state.

In an embodiment of the invention, the transmission mechanism includes an elastic member. When the driving unit drives the carrier to be changed from a first rotation speed to a second rotation speed, the rotating plate rotates relatively to the carrier, and the elastic member is deformed by a deformation amount. The first rotation speed is less than the second rotation speed, and the predetermined rotation speed is between the first rotation speed and the second rotation speed.

In an embodiment of the invention, the rotating plate has a mass center, and the mass center is not located at a rotation center of the rotating plate. The transmission mechanism includes an elastic member, and the elastic member is connected between the rotating plate and the carrier.

In an embodiment of the invention, a weight block is disposed on the rotating plate, the rotating plate combined with the weight block has a mass center, and the mass center is not located at a rotation center of the rotating plate. The transmission mechanism includes an elastic member, and the elastic member is connected between the rotating plate and the carrier.

In an embodiment of the invention, the transmission mechanism includes a sliding block and an elastic member, and the sliding block is connected with the elastic member and the rotating plate.

In an embodiment of the invention, the rotating plate has a gear, the sliding block has a gear rack, and the gear rack is engaged with the gear.

In an embodiment of the invention, the carrier has a guide rod, and the sliding block is slidably disposed on the guide rod.

To sum up, the liquid analyzing device of the invention can control the operation relation between the transmission mechanism and the rotating plate through the different centrifugal forces generated when the carrier rotates in different rotation speeds, such that the rotating plate can rotate relatively to the carrier, thereby, switching the rotating plate between different facing directions. Accordingly, the liquid analyzing device provided by the invention can automatically switch the facing direction of the rotating plate and thereby, effectively improve the operation efficiency.

To make the above features and advantages of the invention more comprehensible, embodiments accompanied with drawings are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

Figure 1:
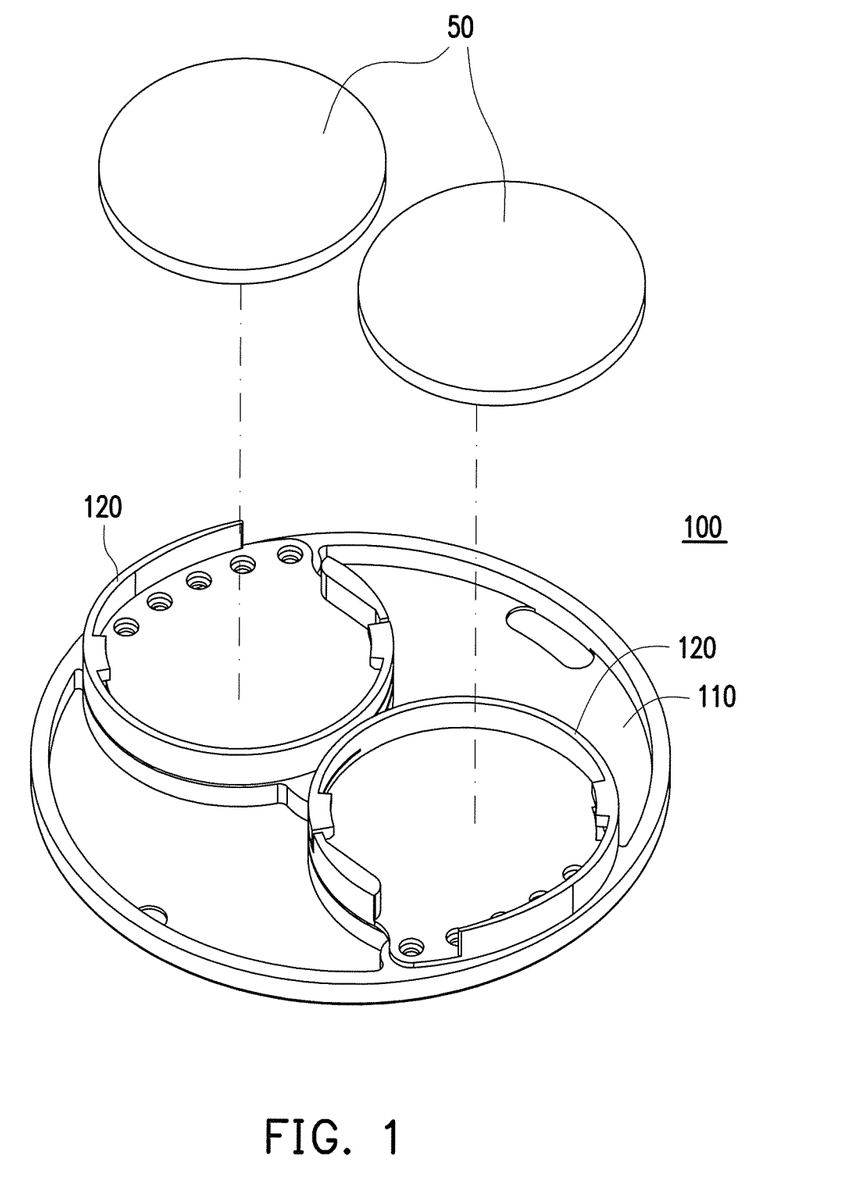
FIG. 1 is a perspective diagram illustrating a liquid analyzing device according to an embodiment of the invention.
Figure 2:
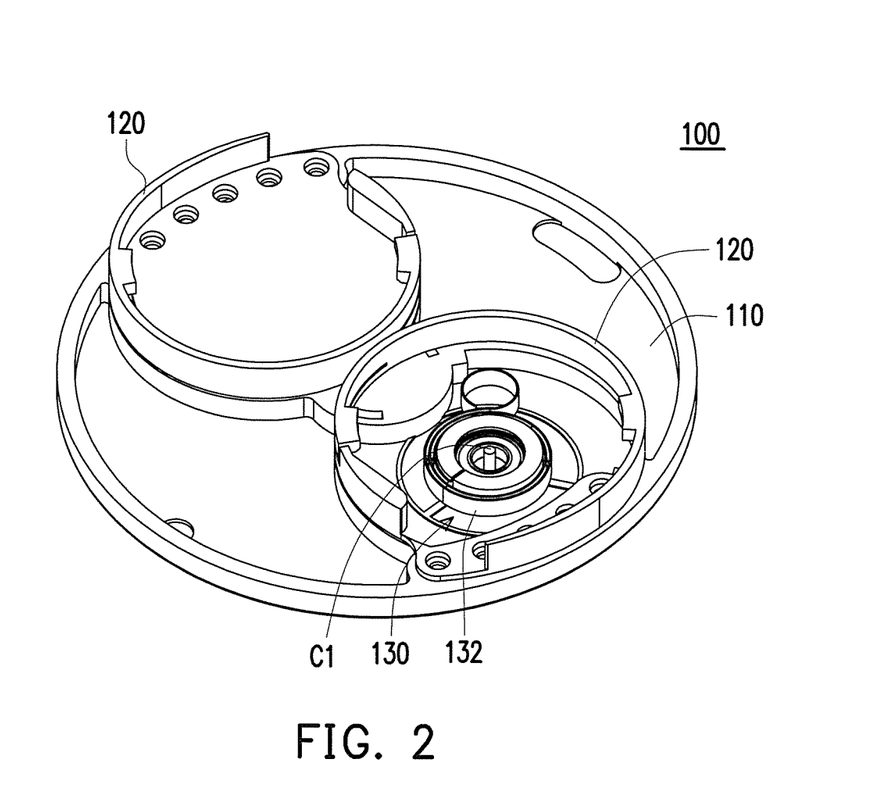
FIG. 2 is a perspective diagram illustrating a portion of components of the liquid analyzing device depicted in FIG. 1.
Figure 3:
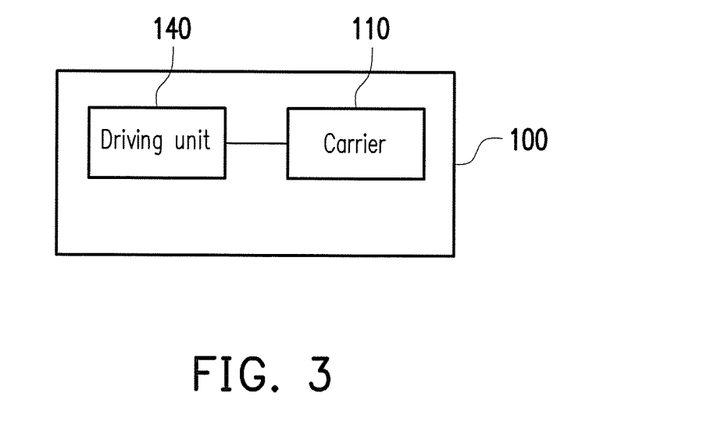
FIG. 3 is a block diagram illustrating a portion of components of the liquid analyzing device depicted in FIG. 1.
Figure 4:
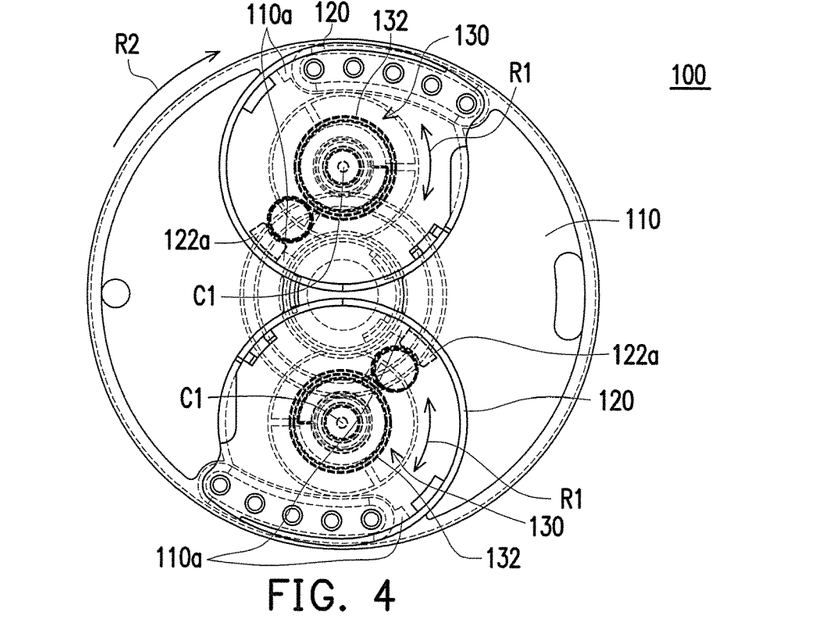
FIG. 4 is a schematic top-view diagram illustrating a portion of components of the liquid analyzing device depicted in FIG. 1, in which the rotating plate is in a first facing state.

FIG. 1 is a perspective diagram illustrating a liquid analyzing device 100 according to an embodiment of the invention. FIG. 2 is a perspective diagram illustrating a portion of components of the liquid analyzing device 100 depicted in FIG. 1. FIG. 3 is a block diagram illustrating a portion of components of the liquid analyzing device 100 depicted in FIG. 1. FIG. 4 is a schematic top-view diagram illustrating a portion of components of the liquid analyzing device 100 depicted in FIG. 1, in which the rotating plate 120 is in a first facing state. Referring to FIG. 1 to FIG. 4, a liquid analyzing device 100 of the present embodiment is, for example, a blood analyzing device and includes a carrier 110, at least one rotating plate 120 (which is illustrated as two), at least one transmission mechanism 130 (which is illustrated as two) and a driving unit 140.

The driving unit 140 is, for example, a motor adapted to drive the carrier 110 to rotate. The rotating plate 120 is rotatably disposed on the carrier 110 and adapted to support an analyzing cassette 50. The analyzing cassette 50 is adapted to contain a liquid (e.g., blood and corresponding medicaments) to be tested. The rotating plate 120 rotates relatively to the carrier 110 around a rotation center C1, and a mass center of the rotating plate 120 is not located at the rotation center C1 of the rotating plate 120. The transmission mechanism 130 includes an elastic member 132, and the elastic element 132 is connected between the carrier 110 and the corresponding rotating plate 120. In the present embodiment, the elastic member 132 is, for example, a torsion spring or a winding spring disposed surrounding the rotation center C1 of the corresponding rotating plate 120, such that the elastic member 132 will extend around a rotation direction R1 of the corresponding rotating plate 120 and have elastic deformation when applying a force on the elastic member 132. The numbers of the rotating plates 120 and the transmission mechanisms 130 are not limited in the invention, which may be respectively illustrated as two as in FIG. 1 or designed as in other adaptive numbers based on demands.

Figure 5:
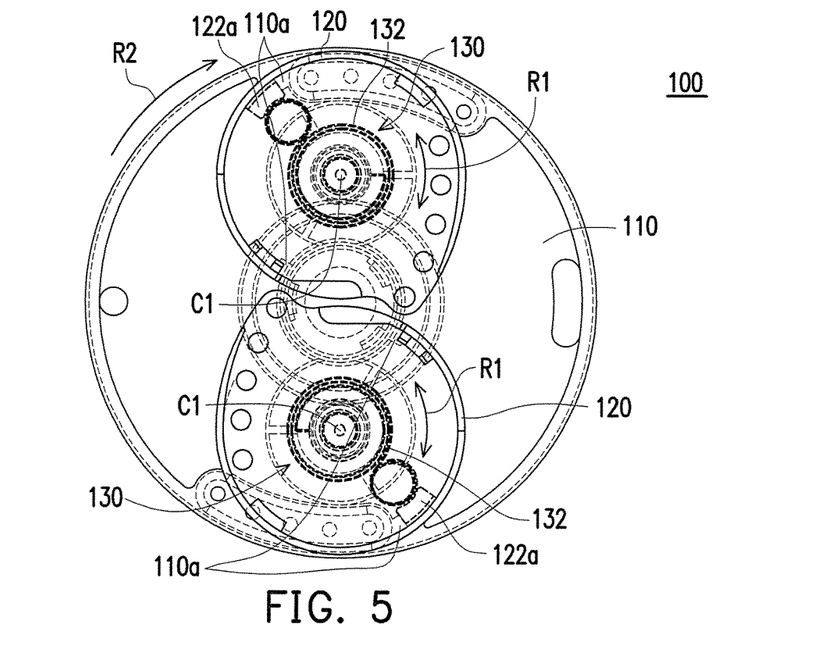
FIG. 5 is a schematic top-view diagram illustrating a portion of components of the liquid analyzing device depicted in FIG. 1, in which the rotating plate is in a second facing state.

The operation of the liquid analyzing device 100 of the invention will be described with reference to the drawings below. Referring to FIG. 4 and FIG. 5, FIG. 5 is another top-view diagram illustrating a portion of components of the liquid analyzing device 100 depicted in FIG. 1, in which the rotating plate 120 is in a second facing state. After the analyzing cassette 50 is placed on the rotating plate 120 of the liquid analyzing device 100, the driving unit 140 first drives the carrier 110 to rotate in a first rotation speed. In this circumstance, the rotating plate 120 on the carrier 110 is in the first facing state as illustrated in FIG. 4, and the elastic member 132 has a first deformed state.

After the carrier 110 rotates in the first rotation speed for a period of time, the driving unit 140 starts to drive the rotation speed of the carrier 110 to be changed and cross a predetermined rotation speed. Specifically, after the carrier 110 rotates in the first rotation speed for the period of time, the driving unit 140 drives the carrier 110 to change from the first rotation speed to a second rotation speed. The predetermined rotation speed is between the first rotation speed and the second rotation speed. In this way, the driving unit 140 drives the rotation speed of the carrier 110 to be changed and cross the predetermined rotation speed.

Additionally, when the driving unit 140 drives the rotation speed of the carrier 110 to be changed and cross the predetermined rotation speed, the change of the rotation speed drives the operation relation between the transmission mechanism 130 and the rotating plate 120, such that the rotating plate 120 rotates relatively to the carrier 110. In this circumstance, the liquid analyzing device 100 is in, for example, a second facing state as illustrated in FIG. 5, and the elastic member 132 has a second deformed state.

In the present embodiment, the mass center of the rotating plate 120 is not located at the rotation center C1 of the rotating plate 120. When the driving unit 140 drives the rotation speed of the carrier 110 to be changed and cross the predetermined rotation speed, the rotating plate 120 is driven to rotate relatively to the carrier 110 through the relation between the change of centrifugal force applied on the mass center of the rotating plate 120 and the elastic force of the elastic member 132 of the transmission mechanism 130.

For instance, it is assumed that the second rotation speed is greater than the first rotation speed, and when the driving unit 140 drives the carrier 110 depicted in FIG. 4 to be changed from the first rotation speed to the second rotation speed and cross the predetermined rotation speed, the centrifugal force generated by the carrier 110 increases, and the centrifugal force applied on the mass center of the rotating plate 120 also increases. When the centrifugal force applied on the mass center of the rotating plate 120 is greater than the elastic force of the elastic member 132 of the transmission mechanism 130, the rotating plate 120 deforms the elastic member 132 and rotate relatively to the carrier 110 along a first direction (e.g., a clockwise direction) for an angle to be in the second facing state as illustrated in FIG. 5. In the meantime, the elastic member 132 is deformed to the second deformed state from the first deformed state. The elastic member 132 can be deformed by compressing or extending according to the force direction applied on the elastic member 132.

Otherwise, when the driving unit 140 drives the carrier 110 depicted in FIG. 5 to be changed from the second rotation speed to the first rotation speed to cross the predetermined rotation speed, the centrifugal force generated by the carrier 110 decreases, and the centrifugal force applied on the mass center of the rotating plate 120 also decreases. When the centrifugal force applied on the mass center of the rotating plate 120 is less than the elastic force of the elastic member 132 of the transmission mechanism 130, the rotating plate 120 is pushed by the elastic member 132 to rotate relatively to the carrier 110 along a second direction (e.g., a counterclockwise direction) opposite to the first direction to be in the first facing state as illustrated in FIG. 4. In the meantime, the elastic member 132 returns to the first deformed state from the second deformed state.

In the embodiments of the invention, the centrifugal force generated by the carrier 110 when rotating in the predetermined rotation speed is equivalent to the elastic force of the elastic member 132 of the transmission mechanism 130.

Specifically, when the driving unit 140 drives the carrier 110 to rotate in the second rotation speed which is greater than the predetermined rotation speed, the centrifugal force generated by the carrier 110 is greater than the elastic force of the elastic member 132, and thus, the rotating plate 120 deforms the elastic member 132 and rotates relatively to the carrier 110, such that the elastic member 132 has a deformation amount and is deformed to the second deformed state from the first deformed state. In this circumstance, the rotating plate 120 is in the second facing state as illustrated in FIG. 5. On the contrary, when the driving unit 140 drives the carrier 110 to rotate in the first rotation speed less than the predetermined rotation speed, the centrifugal force generated by the carrier 110 is less than the elastic force of the elastic member 132, and thus, the rotating plate 120 is incapable of deforming the elastic member 132, and the elastic member 132 returns to the first deformed state from the second deformed state. In this circumstance, the rotating plate 120 is in the first facing state as illustrated in FIG. 4.

In an embodiment, the first rotation speed and the second rotation speed are 2000 rpm and 4000 rpm, respectively, or other adaptive different rotation speeds, which are not limited in the invention. In addition, in other embodiments, a weight block may be disposed on the rotating plate 120, such that the mass center of the rotating plate 120 combined with the weight block is not located at the rotation center of the rotating plate 120.

As described above, the liquid analyzing device 100 provided by the embodiments of the invention controls the operation relation between the transmission mechanism 130 and the rotating plate 120 through the different centrifugal forces generated when the carrier rotates in different rotation speeds, such that the rotating plate 120 rotates relatively to the carrier 110, thereby, switching the rotating plate 120 between different facing directions, such as the first facing state as illustrated in FIG. 4 and the second facing state as illustrated in FIG. 5. Accordingly, the liquid analyzing device 100 provided by the embodiments of the invention is capable of automatically switching the facing direction of the rotating plate 120 and thereby, effectively improves the operation efficiency.

In the present embodiment, the carrier 110 rotates in a single direction, for example. Namely, the carrier 110 has the same rotation direction R2 when rotating in the first rotation speed and the second rotation speed, but the invention is not limited thereto. In addition, when the driving unit 140 drives the carrier 110 to rotate, for example, in the first rotation speed and the second rotation speed alternately, the facing direction of the rotating plate 120 will be continuously switched between the first facing state as illustrated in FIG. 4 and the second facing state as illustrated in FIG. 5 alternately during the process of the rotation speed of the carrier 110 being changed, such that the needed time for mixing blood and medicaments will be effectively decreased.

In the present embodiment, the carrier 110 has at least one first stop structure 110a (which is illustrated as two), the rotating plate 120 has at least one second stop structure 122a (which is illustrated as two), and the second stop structures 122a are limited to moving along with the rotating plate 120 between the two first stop structures 110a. Namely, a range of the rotating plate 120 rotating relatively to the carrier 110 may be limited by the interference from the first stop structures 110a and the second stop structures 122a.

Figure 6:
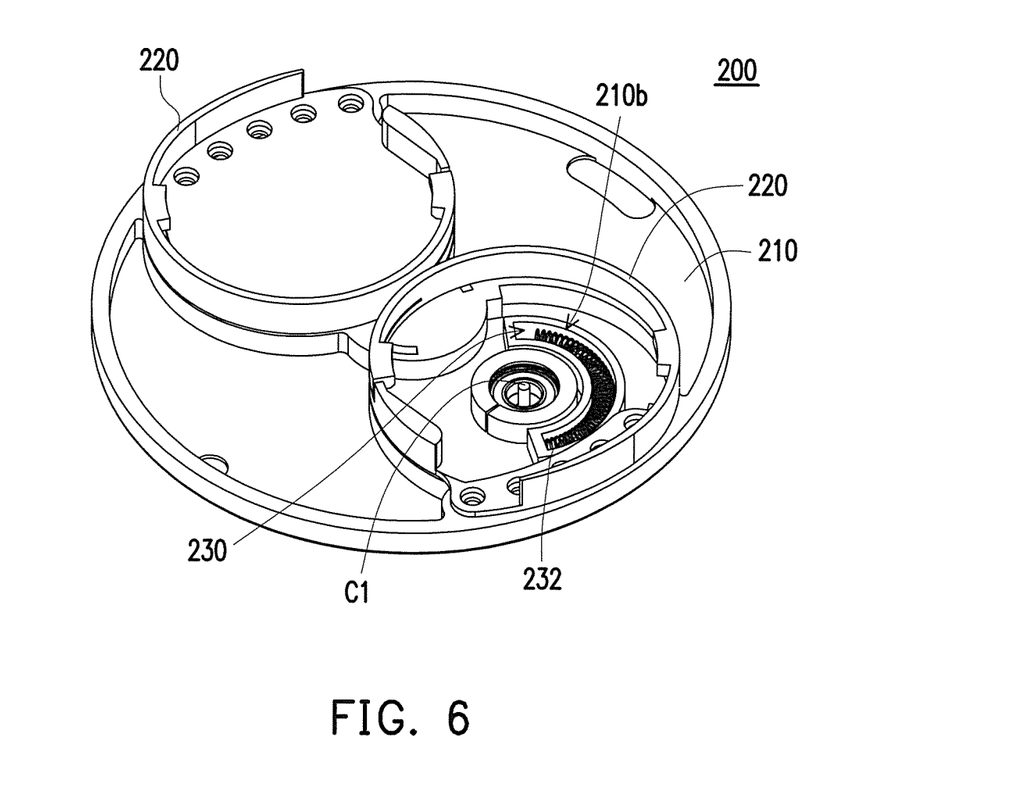
FIG. 6 is a perspective diagram illustrating a liquid analyzing device according to another embodiment of the invention.
Figure 7:
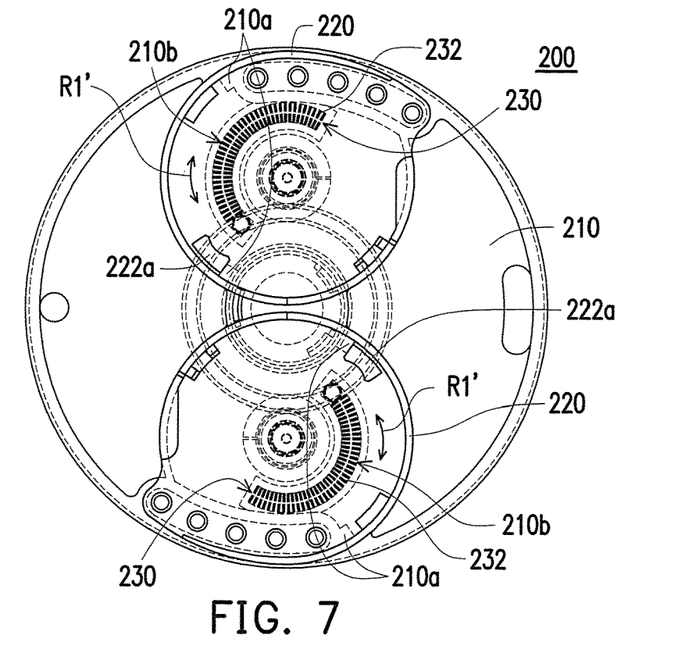
FIG. 7 is a schematic top-view diagram illustrating a portion of components of the liquid analyzing device depicted in FIG. 6, in which the rotating plate is in a first facing state.
Figure 8:
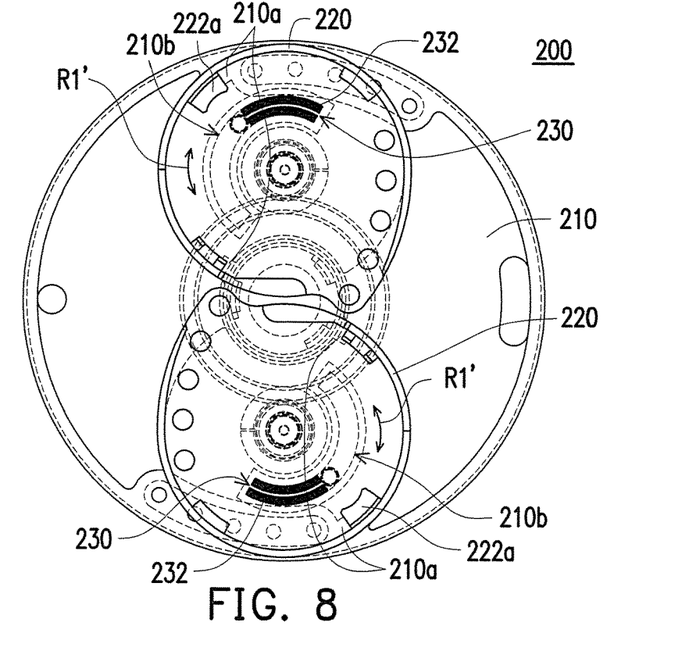
FIG. 8 is a schematic top-view diagram illustrating a portion of components of the liquid analyzing device depicted in FIG. 6, in which the rotating plate is in a second facing state.

FIG. 6 is a perspective diagram illustrating a portion of components of a liquid analyzing device 200 according to another embodiment of the invention. FIG. 7 is a schematic top-view diagram illustrating a portion of components of the liquid analyzing device 200 depicted in FIG. 6, in which a rotating plate 220 is in a first facing state. FIG. 8 is a schematic top-view diagram illustrating a portion of components of the liquid analyzing device 200 depicted in FIG. 6, in which the rotating plate 220 is in a second facing state. In the liquid analyzing device 200 illustrated in FIG. 6 to FIG. 8, the operations of a carrier 210, first stop structures 210a, a rotating plate 220, second stop structures 222a, a transmission mechanism 230 and an elastic member 232 are similar to the operations of the carrier 110, the first stop structures 110a, the rotating plate 120, the second stop structures 122a, the transmission mechanism 130 and the elastic member 132 of the liquid analyzing device 100 illustrated in FIG. 1 to FIG. 5.

The liquid analyzing device 200 is different from the liquid analyzing device 100 in that the elastic member 232 is a telescopic spring, instead of a torsion spring or a winding spring. In addition, the carrier 210 has a guide slot 210b, the guide slot 210b extends around a rotation direction R1' of the rotating plate 220, and the elastic member 232 is located in the guide slot 210b to be adapted to generate elastic deformation along the rotation direction of the rotating plate 220. In the present embodiment, the liquid analyzing device 200 may also control the operation relation between the transmission mechanism 230 and the rotating plate 220 by changing the rotation speed of the carrier 210, thereby, switching the rotating plate 120 between different facing directions as illustrated in FIG. 7 and FIG. 8, which will not be repeated.

Figure 9:
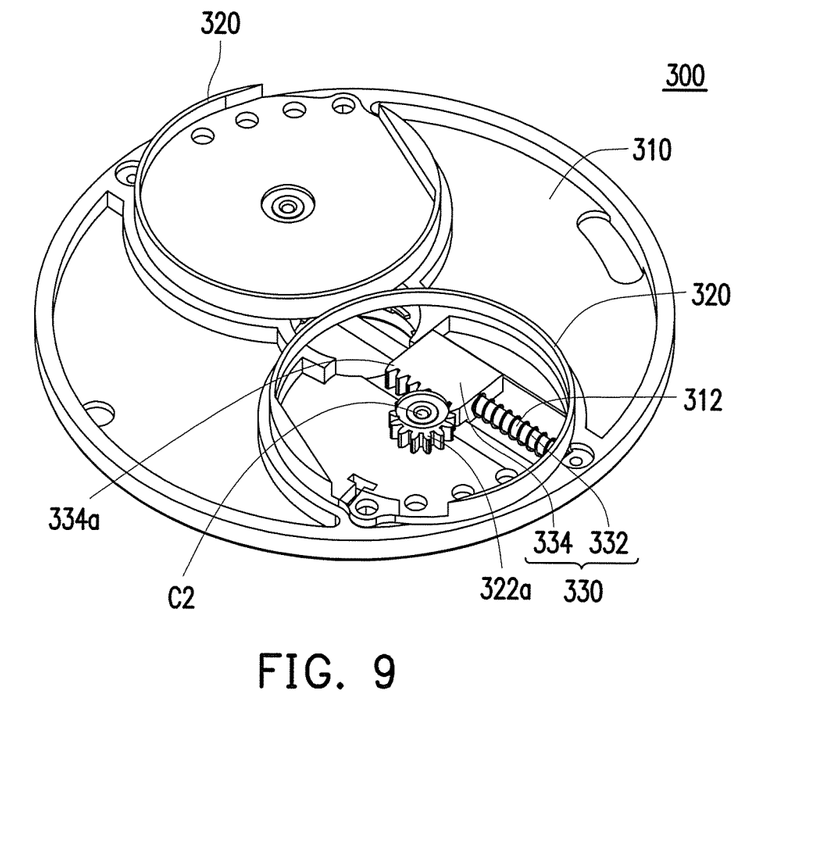
FIG. 9 is a perspective diagram illustrating a portion of components of a liquid analyzing device according to another embodiment of the invention.
Figure 10:
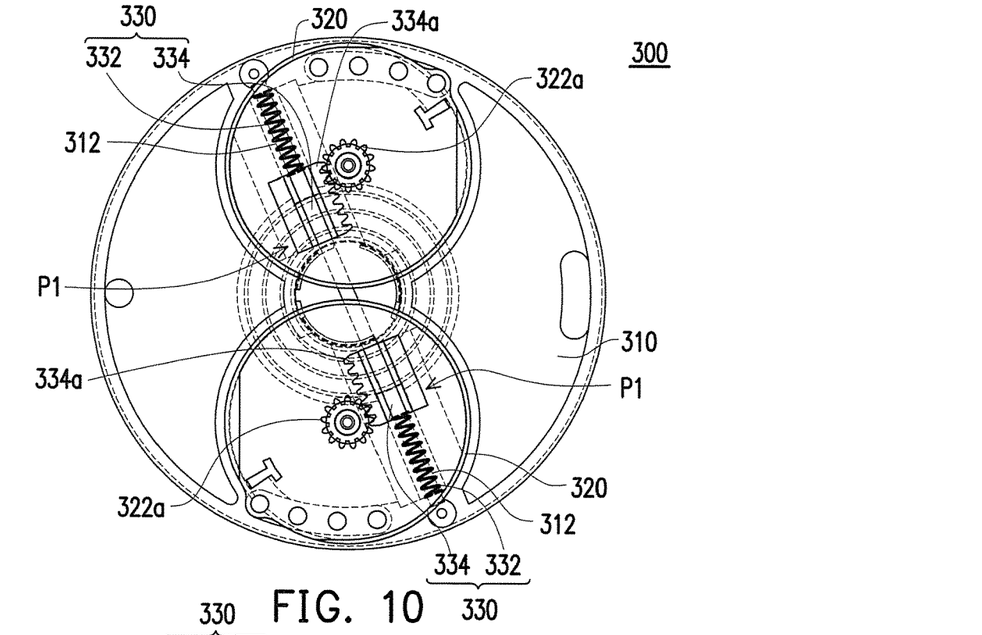
FIG. 10 is a schematic top-view diagram illustrating a portion of components of the liquid analyzing device depicted in FIG. 9, in which the rotating plate is in a first facing state.
Figure 11:
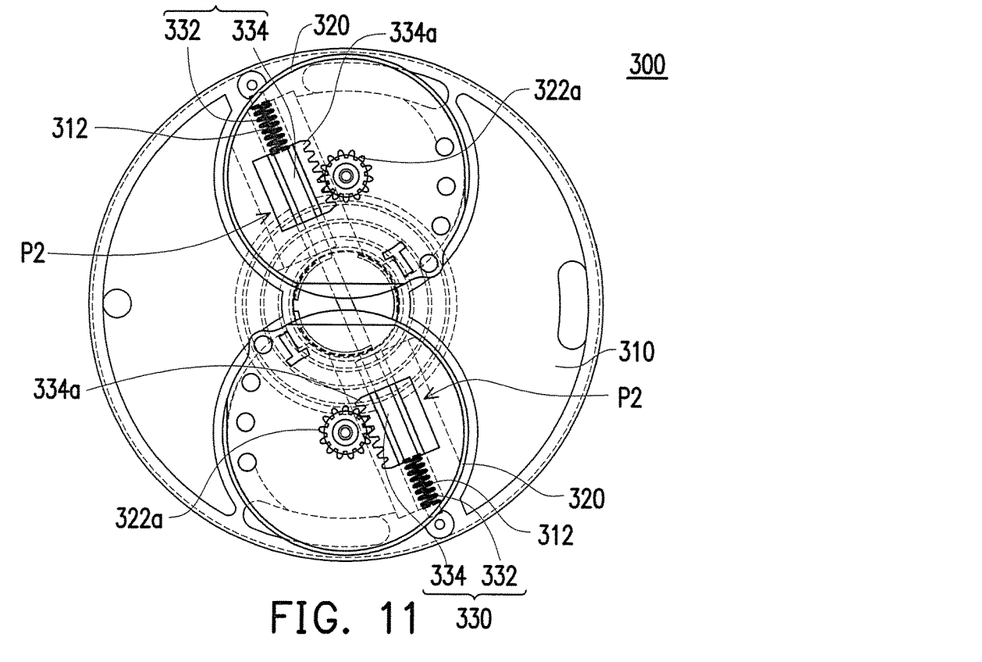
FIG. 11 is a schematic top-view diagram illustrating a portion of components of the liquid analyzing device depicted in FIG. 9, in which the rotating plate is in a second facing state.

FIG. 9 is a perspective diagram illustrating a portion of components of a liquid analyzing device 300 according to another embodiment of the invention. FIG. 10 is a schematic top-view diagram illustrating a portion of components of the liquid analyzing device 300 depicted in FIG. 9, in which a rotating plate 320 is in a first facing state. FIG. 11 is a schematic top-view diagram illustrating a portion of components of the liquid analyzing device 300 depicted in FIG.

9, in which the rotating plate 320 is in a second facing state. In the liquid analyzing device 300 illustrated in FIG. 9 to FIG. 11, the connecting relation between a carrier 310 and a rotating plate 320 is similar to the connecting relation between the carrier 110 and the rotating plate 120 of the liquid analyzing device 100 illustrated in FIG. 1 to FIG. 5.

The liquid analyzing device 300 is different from the liquid analyzing device 100 in that a transmission mechanism 330 includes not only an elastic member 332 but also a sliding block 334. The sliding block 334 abuts against the elastic member 332 and is connected with the rotating plate 320. In the present embodiment, the carrier 310 has a guide rod 312. The sliding block 334 has a gear rack 334a and is slidably disposed on the carrier guide rod 312. The rotating plate 320 has a gear 322a in its rotation center C2, and the gear rack 334a of the sliding block 334 is engaged with the gear 332a of the rotating plate 320. The elastic member 332 is connected between the sliding block 334 and the carrier 310 and sleeves the guide rod 312.

In the present embodiment, when the rotation speed of the carrier 310 is changed, the sliding block 334 moves due to the change of the relation between the centrifugal force and the elastic force of the elastic member 332, so as to drive the rotating plate 320 to rotate.

For instance, in a scenario that the rotating plate 320 is in the first facing state as illustrated in FIG. 10, when the rotation speed of the carrier 310 is changed from the first rotation speed to the second rotation speed and crosses the predetermined rotation speed, the centrifugal force generated due to the rotation speed of the carrier 310 increases, and the centrifugal force applied on the sliding block 334 also increases. When the centrifugal force applied on the sliding block 334 is greater than the elastic force of the elastic member 332, the sliding block 334 deforms the elastic member 332 and slides from a first position P1 illustrated in FIG. 10 to a second position P2 illustrated in FIG. 11. In this process, the sliding block 334 drives the rotating plate 320 to rotate by means of the engagement relation between the gear rack 334a and the gear 332a, such that the rotating plate 320 rotates relatively to the carrier 310 to the second facing state as illustrated in FIG. 11. In the meantime, the elastic member 332 is deformed to the second deformed state from the first deformed state.

On the contrary, when the rotation speed of the carrier 310 depicted in FIG. 11 is changed from the second rotation speed to the first rotation speed and crosses the predetermined rotation speed, the centrifugal force generated due to the rotation speed of the carrier 310 decreases, and the centrifugal force applied on the sliding block 334 also decreases. When the centrifugal force applied on the sliding block 334 is less than the elastic force of the elastic member, the sliding block 334 is pushed by the elastic member 332 and slides from the second position P2 illustrated in FIG. 11 to the first position P1 illustrated in FIG. 10. In this process, the sliding block 334 drives the rotating plate 320 to rotate by means of the engagement relation between the gear rack 334a and the gear 332a, such that the rotating plate 320 rotates relatively to the carrier 310 to the first facing state as illustrated in FIG. 10. In the meantime, the elastic member 332 returns to the first deformed state from the second deformed state.

Based on the above, the liquid analyzing device of the invention can control the operation relation between the transmission mechanism and the rotating plate through the different centrifugal forces generated when the carrier rotates in different rotation speeds, such that the rotating plate rotates relatively to the carrier, thereby, switching the rotating plate between different facing directions. Accordingly, the liquid analyzing device provided by the invention can automatically switch the facing direction of the rotating plate, such that the operation efficiency can be effectively improved.

Although the invention has been disclosed by the above embodiments, they are not intended to limit the invention. It will be apparent to one of ordinary skill in the art that modifications and variations to the invention may be made without departing from the spirit and scope of the invention. Therefore, the scope of the invention will be defined by the appended claims.

What is claimed is:

1. A liquid analyzing device, comprising:
    a carrier;
    a driving unit, adapted to drive the carrier to rotate;
    a rotating plate, rotatably disposed on the carrier and adapted to support an analyzing cassette; and
    a transmission mechanism, comprising a sliding block and an elastic member, and the sliding block is connected with the elastic member and the rotating plate,
    wherein when the driving unit drives the carrier to rotate to enable a rotation speed of the carrier to be changed and cross a predetermined rotation speed, the sliding block moves due to change of the relation between the centrifugal force and the elastic force of the elastic member so as to drive the rotating plate to rotate relatively to the carrier.

2. The liquid analyzing device according to claim 1, wherein when the driving unit drives the carrier to be changed from a first rotation speed to a second rotation speed or from the second rotation speed to the first rotation speed, the rotating plate rotates relatively to the carrier, wherein the predetermined rotation speed is between the first rotation speed and the second rotation speed.

3. The liquid analyzing device according to claim 2, wherein when the carrier is changed from the first rotation speed to the second rotation speed, the rotating plate rotates relatively to the carrier along a first direction, and when the carrier is changed from the second rotation speed to the first rotation speed, the rotating plate rotates relatively to the carrier along a second direction, wherein the second direction is opposite to the first direction.

4. The liquid analyzing device according to claim 1, wherein when the rotation speed of the carrier is less than the predetermined rotation speed, the elastic member has a first deformed state and the carrier is in a first facing state, and when the rotation speed of the carrier is greater than the predetermined rotation speed, the elastic member has a second deformed state and the carrier is in a second facing state, wherein the second facing state refers to the rotating plate rotating relatively to the carrier for an angle from the first facing state, and the second deformed state refers to the elastic member being deformed by a deformation amount from the first deformed state.

5. The liquid analyzing device according to claim 1, wherein when the driving unit drives the carrier to be changed from a first rotation speed to a second rotation speed, the rotating plate rotates relatively to the carrier and the elastic member is deformed by a deformation amount, wherein the first rotation speed is less than the second rotation speed, and the predetermined rotation speed is between the first rotation speed and the second rotation speed.

6. The liquid analyzing device according to claim 1, wherein the rotating plate has a gear, the sliding block has a gear rack, and the gear rack is engaged with the gear.

7. The liquid analyzing device according to claim 1, wherein the carrier has a guide rod, and the sliding block is slidably disposed on the guide rod.

\* \* \* \* \*